(12) United States Patent
Thomalla et al.

(10) Patent No.: US 7,610,796 B2
(45) Date of Patent: Nov. 3, 2009

(54) METHOD FOR ADJUSTING SPECIFIC QUALITY CHARACTERISTICS AND PROPERTIES OF PIPES BY MEANS OF A PRESSURE TEST

(75) Inventors: Siegfried Thomalla, Hilchenbach (DE); Franz-Josef Schmeck, Freudenberg (DE); Hans-Joachim de la Camp, Gröbenzell (DE)

(73) Assignee: Eisen- und Metallwerke Ferndorf GmbH, Kreuztal-Ferndorf (DE)

( * ) Notice: Subject to any disclaimer, the term of this patent is extended or adjusted under 35 U.S.C. 154(b) by 93 days.

(21) Appl. No.: 10/577,190

(22) PCT Filed: Aug. 13, 2004

(86) PCT No.: PCT/EP2004/009128

§ 371 (c)(1),
(2), (4) Date: Jan. 16, 2007

(87) PCT Pub. No.: WO2005/046904

PCT Pub. Date: May 26, 2005

(65) Prior Publication Data

US 2007/0143049 A1    Jun. 21, 2007

(30) Foreign Application Priority Data

Oct. 25, 2003    (DE) .................. 103 50 279

(51) Int. Cl.
*G01M 3/04* (2006.01)
(52) U.S. Cl. .................................... 73/49.5
(58) Field of Classification Search .............. 73/49.5; 72/61, 54

See application file for complete search history.

(56) References Cited

U.S. PATENT DOCUMENTS

| | | | | |
|---|---|---|---|---|
| 1,870,009 A * | 8/1932 | Huet | .............. | 122/33 |
| 2,667,136 A * | 1/1954 | Singer et. al. | .............. | 72/62 |
| 3,303,680 A * | 2/1967 | Thielsch | .............. | 72/58 |
| 4,130,925 A * | 12/1978 | Gibson | .............. | 405/174 |
| 5,303,570 A * | 4/1994 | Kaiser | .............. | 72/62 |
| 5,737,953 A * | 4/1998 | Allison et al. | .............. | 72/58 |
| 5,953,945 A * | 9/1999 | Horton | .............. | 72/58 |
| 6,601,423 B1 * | 8/2003 | Peterson | .............. | 72/58 |

* cited by examiner

*Primary Examiner*—Hezron Williams
*Assistant Examiner*—Gunnar J Gissel
(74) *Attorney, Agent, or Firm*—Friedrich Kueffner

(57) ABSTRACT

The invention relates to a method for adjusting specific quality characteristics and/or properties of pipes (1) by means of a pressure test, especially for steel pipes of pipe conduits for combustible media. According to said method, in addition to the water volume required for the pressure test according to DIN EN 10208 part 2, an additional water volume (12) is filled into every single pipe (1) with the proviso that the pipe material is slightly subjected to plastic stress.

5 Claims, 1 Drawing Sheet

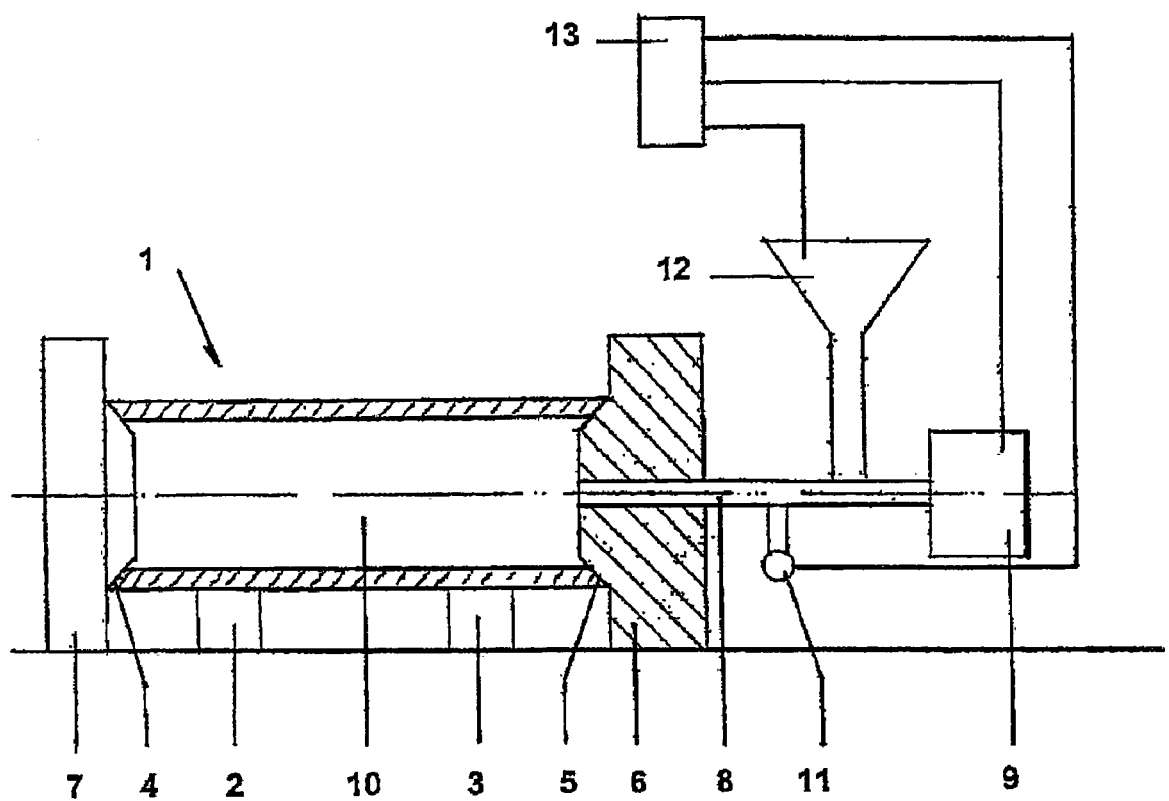

METHOD FOR ADJUSTING SPECIFIC QUALITY CHARACTERISTICS AND PROPERTIES OF PIPES BY MEANS OF A PRESSURE TEST

For conveying combustible media, such as for example natural gas or crude oil, pipelines and especially long-distance pipelines are placed aboveground or belowground over large distances. The steel pipes actually used for this purpose have diameters of up to 1,800 mm, depending on the intended flow quantities.

Used in this connection are seamless pipes (S-pipes), high frequency welded pipes (HFW-pipes), submerged arc welded pipes (SAW-pipes) or steel pipes which are manufactured by means of a combined submerged arc and controlled atmosphere welding (COW-pipes) method.

In submerged arc welded pipes, a distinction is made between pipes having a longitudinal seam (SAWL) or a helical seam (SAWH).

The technical requirements for delivering such steel pipes are stated in DIN EN 10208, part 2. In accordance with paragraph 8.2.3.8, an internal pressure test is to be carried out with water. The purpose of this internal pressure test is to determine whether the pipe will withstand the hydrostatic testing pressure. The magnitude of the hydrostatic testing pressure depends on the type of testing apparatus.

For manufacturing pipelines, the above-described steel pipes are welded together while taking into consideration their different lengths. After the pipelines are manufactured, they are subjected to a stress test if the pipes are used for conveying hazardous liquids or gases under high pressures. Stress tests are hydraulic pressure tests with loads acting on the pipes and curved pipes up to the range of the actual yield strength of the pipes with a sufficient margin to the resistance to breakage, while taking into consideration the permissible integral plastic deformation of the pipeline.

VdTÜV Merkblatt [information sheet] 1060 (pipelines) contains instructions for the use and procedure of the stress test.

This time sequence including manufacture of the pipe in the manufacturing plant, pressure tests according to DIN EN 10208 part 2 in the manufacturing plant, transport of the pipes to the placement location, welding of the pipes and carrying out the stress tests according to VdTÜV, instruction sheet 1060, has the disadvantage that the pipe may be plastically deformed during the stress test and defects which are already present during the manufacture of the pipes, such as cracks or the like, are only now determined in a welded pipeline. In the case of a defect which occurs only during the stress test, this operational sequence results in a time consuming and expensive repair of the pipeline.

Therefore, the invention is based on the object of reducing the stress test on location and to improve the quality characteristics and/or properties of the pipes.

In accordance with the invention, the object is met by a method having the features recited in claim 1.

Due to the slight strain acting on the pipe in the plastic range already in the manufacturing plant, following the pressure test according to DIN EN 10208 part 2, the steps to be taken at the placement location of the pipeline during a stress test are already reduced significantly and the risk of welding a defective pipe to the pipeline is minimized.

Since the plastic deformation of the individual pipes is already carried out during the manufacture in the manufacturing plant, a pipe is delivered to the placement location which is already pretreated with respect to this change.

The internal expansion, carried out in accordance with the invention, further results in:

- an optimization of the circular shape which results in a small misalignment of the edges;
- a reduction of internal stresses;
- a reduction of the scattering of the yield strength over the entire pipeline by raising the actual yield strength of the pipes with low K×S values, so that a higher permissible load change is achieved;
- optimal behavior of the pipes during the hydraulic pressure test in the field (=stress test), because the pipes manufactured according to the invention are listed in the column "non-expanded pipes with proven pressure relief" in accordance with VdTÜV, sheet pipelines, 1060;
- a reduction of pressure peaks in the area of shape deviations (roof formation, flattening . . . );
- the external diameters of the pipes are increased by the additional water volume by 0.2-0.3%;
- loading of the pipes during the modified hydraulic pressure test is usually higher than during the stress test when erecting the pipelines;
- greater vertical differences which occur during the placement of the pipelines in the field can be overcome during the pressure test;
- utilization of the permissible water volume according to VdTÜV, sheet 1060, for the cold hardening of the pipes in a pipeline during the stress test is not necessary for shape deviations when using the pipes according to the invention, so that higher testing pressures become possible, particularly with respect to later pressure increases in the pipeline during operation.

Embodiments of the invention are being described in more detail with the aid of very schematic drawings. In the drawing FIG. 1 shows a pipe testing apparatus in a side view in partial section.

FIG. 1 shows a pipe 1 which is being subjected to an internal pressure test. For this purpose, the pipe 1 is placed onto two support points 2, 3 and is closed at both ends 4, 5 with conically shaped tensioning elements 6, 7. Water is pumped by a pump 9 into the interior 10 of the pipe 1 through an opening 8 in the tensioning element 6 and the pipe 1 is subjected to a hydrostatic pressure test.

The pressure to be taken into consideration during the pressure test, which is in the same order of magnitude of the actually statistically determined K×S values, is controlled and/or adjusted by a measuring apparatus 11. After the predetermined testing pressure has been reached, this pressure is maintained constant for a period of time.

For adjusting specific quality characteristics and/or properties, a previously computed additional water quantity 12 is subsequently pumped into the pipe 1. The pumping process for the additional water quantity 12 takes place over a period of time of several minutes. Depending on the type of pipe and in dependence on the thickness of the wall of the pipe, the length of the pipe, the pipe diameter and the material properties, 3 to 10 minutes must be allowed for the pumping process 3.

For determining the material properties, the initial material of the steel pipes is subjected to a tension test. Moreover, the values which must be provided by the rolling mill, are taken into consideration.

By adding this additional water quantity 12 over a predetermined period of time, a plastic deformation of the pipe 1 is achieved. In order to facilitate a plastic deformation for the pipe 1, it is also possible to take into consideration a dwell time of the entire water quantity in the pipe 1. This additional dwell time can be determined previously in a test pipe or at the beginning of the production at the first pipes of a series.

All data with respect to the manufactured pipe, the results of the pressure test, the additional water quantity, the pumping time, the dwell time, etc, are recorded and documented in a connected computer 13.

The invention claimed is:

1. A method for adjusting specific quality characteristics and/or properties of steel pipe by pressure testing, comprising the steps of:
   pumping water into an interior of the steel pipe;
   conducting a hydrostatic pressure test pursuant to DIN EN 10208 Part 2 using the pumped-in water; and
   pumping a predetermined additional volume of water into the steel pipe ongoing from the hydrostatic pressure test so that the steel pipe is slightly stressed in the plastic range.

2. Method according to claim 1, wherein the method includes adjusting specific quality characteristics and/or properties of steel pipe for pipelines for combustible media.

3. Method according to claim 1, wherein the additional water volume remains in the pipe for a period of 2 to 3 mm.

4. Method according to claim 1, wherein the pipe is enlarged at the outer diameter by 0.2 to 0.3%.

5. Method according to claim 1, wherein the additional water volume which is taken into consideration as an intended value is determined by filling in a step by step manner an additional water volume into a test pipe until the changes reach a previously determined limit value.

* * * * *